United States Patent [19]
Ferguson et al.

[11] Patent Number: 5,637,086
[45] Date of Patent: Jun. 10, 1997

[54] METHOD OF DELIVERING A THERAPEUTIC AGENT OR DIAGNOSTIC DEVICE USING A MICRO OCCLUSION BALLOON CATHETER

[75] Inventors: Robert D. G. Ferguson, Memphis, Tenn.; Sandra G. Tartaglino, Canton, Mass.

[73] Assignee: Boston Scientific Corporation, Natick, Mass.

[21] Appl. No.: 525,318

[22] Filed: Sep. 7, 1995

Related U.S. Application Data

[63] Continuation of Ser. No. 235,373, Apr. 29, 1994, abandoned.

[51] Int. Cl.⁶ .................................................. A61M 31/00
[52] U.S. Cl. ........................................ 604/53; 604/102
[58] Field of Search .............................. 604/49, 53, 96, 604/101, 102; 606/192, 194

[56] References Cited

U.S. PATENT DOCUMENTS

| | | | |
|---|---|---|---|
| 4,777,951 | 10/1988 | Cribier et al. | 604/96 X |
| 4,819,751 | 4/1989 | Shimada et al. | 606/194 |
| 4,867,742 | 9/1989 | Calderon | 604/28 |
| 4,909,258 | 3/1990 | Kuntz et al. | 604/102 X |
| 5,163,906 | 11/1992 | Ahmadi | 604/101 |
| 5,188,596 | 2/1993 | Condon et al. | 604/101 |
| 5,334,143 | 8/1994 | Carroll | 604/54 |
| 5,489,271 | 2/1996 | Andersen | 604/102 |

*Primary Examiner*—Corrine M. McDermott
*Attorney, Agent, or Firm*—Luke R. Dohmen

[57] ABSTRACT

A micro occlusion balloon catheter and methods for use and manufacture thereof, comprising an elongate member having a proximal and a distal end and a first and second lumen connected to said proximal end. The first lumen communicates with an occlusion balloon located at the distal end of the elongate member. The second lumen extends the entire length of the elongate member and allows for the placement of the catheter over a guidewire. Second lumen 15, communicates with infusion opening 17, located distal to occlusion balloon 16. A further embodiment comprises a third lumen connected to the proximal end of the elongate member. The third lumen may communicate with an infusion port located either proximally or distally to the occlusion balloon. In a still further embodiment the first lumen, the inflation/deflation balloon lumen, of the two lumen embodiment may be adapted to receive a removable stiffening stylet to ease insertion. In the three lumen embodiment, lumen one, the inflation/deflation balloon lumen, and/or the second or third infusion lumens may be proportioned so as to receive stiffening stylets.

3 Claims, 6 Drawing Sheets

METHOD OF DELIVERING A THERAPEUTIC AGENT OR DIAGNOSTIC DEVICE USING A MICRO OCCLUSION BALLOON CATHETER

This is a continuation of application Ser. No. 08/235,373, filed on Apr. 29, 1994, now abandoned.

BACKGROUND OF THE INVENTION

This invention relates in general to balloon catheters and more specifically to micro occlusion balloon catheters.

Balloon catheters have been in existence for many years and have found wide application. In general they are used whenever the occlusion of a vessel is desired such as during embolization, arteriography, preoperative occlusion, emergency control of hemorrhage, chemotherapeutic drug infusion and renal opacification procedures.

The earliest developed and perhaps the most widely used occlusion balloon catheter is a urinary catheter wherein the balloon is used for anchorage. In the 1950's occlusion balloon catheters were introduced for controlling hemorrhage, thrombosing vessels and purposeful infarction. Embolectomy/thrombectomy balloon catheters were introduced in the mid 1960's and the cardiac monitoring catheters came on the market in the 1970's.

The aforementioned catheters unfortunately have limited application. They are single lumen catheters which are only able to occlude and more importantly, they are only able to occlude large vesssels. They do not fit into small diameter vessels and may not be used for the delivery of a therapeutic and/or diagnostic agent.

To achieve both occlusion and delivery of a diagnostic and/or therapeutic agent, the prior art resorted to the use of side by side catheters or calibrated leak balloon catheters, which are a type of flow guided micro catheter. Simultaneous use of two catheters carries the inherent risk of vessel damage and thrombus formation. Moreover, their use is restricted to large diameter vessels which could accommodate two catheters. Thus there still remains the general need for a micro occlusion balloon catheter and specifically for a micro occlusion balloon catheter which has the capacity to occlude small vessels as well as infuse diagnostic and/or therapeutic agents. Hence, the development of calibrated balloon catheters. Unfortunately they too only offered a partial solution.

Calibrated leak balloon catheters were first developed in the mid 1970's by Dr. Charles Kerber. They were used in general for the treatment of cerebral vascular malformations and fistulae and specifically for the therapeutic embolization of distally located cerebrovascular lesions. These catheters comprised a single lumen with a small latex balloon attached to the catheter tip via ligature or cement. For use, the balloon was punctured in the dome with a small gauge needle to allow for the transient expansion of the balloon. Pressurization of the balloon allowed the injectate to be released. This type of catheter had two major advantages. First, when used in conjunction with an extracorporeal propulsion chamber, the antegrade intravascular displacement was assisted by blood flow. Second, it permitted injection of therapeutic embolization material while flow was reduced or stopped making for a more controlled and hence safe delivery method.

Unfortunately, however, this system as well had drawbacks. Balloon inflation could only be maintained during injection. Moreover, inflation was difficult to modulate and control because the degree of inflation was unavoidably related to the pressure of the injection and the size of the hole made by puncturing of the balloon dome. This resulted in vessel rupture, inconsistent rate and volume delivery of injectate, and clogging of the balloon puncture site with embolization material precipitating balloon rupture or failure of deflation. Still further, only liquid and/or small particles, less than approximately 250 micra in diameter, could be delivered therethrough. Still further, these catheters had the inherent drawbacks of flow directed micro catheters in general. They were subject to reduced structural integrity due to diminished catheter wall thickness and weight. This drawback led to catheter rupture, tearing or fracture. In addition, the diminished wall thickness impeded steering of the catheter during insertion which could not be remedied with the use of guidewires.

Thus there still remains the need for a structurally sound micro occlusion balloon catheter which makes controlled balloon inflation and hence occlusion possible. Moreover, there still exists the need for a structurally sound micro occlusion balloon catheter which has the capacity to occlude small vessels as well as infuse diagnostic and/or therapeutic agents. Still further, there exists the need for a structurally sound micro occlusion balloon catheter which allows for the delivery of a wide variety of therapeutic and/or diagnostic agents, including liquid and solid agents.

Large two lumen occlusion balloon catheters which allow for occlusion and the delivery of therapeutic and/or diagnostic agents are known in the art. Yet because of their size, their use is restricted to vessels having a 5–6 mm or greater diameter. Vessels which are between 1.5–5 mm in diameter have heretofore been unpenetratable by two lumen occlusion balloon catheters. Their size and configuration have made access impossible because the catheter must be simultaneously small and flexible in order to follow the tortuous path of micro vessels, yet stiff enough to allow for the insertion and advancement of the catheter to the target site in the vessel path. Notably the target site may be many feet away from the insertion site. Typical micro vessels are the cerebral, renal, coronary and hepatic vasculature.

Dilitation micro balloon catheters, as distinguished from occlusion balloon catheters, having two or three lumens are known in the art. However, as their name implies, they dilate vessels and as such cause damage to vessels. Occlusion balloon catheters on the otherhand, occlude blood flow only and do not dilate the vessels. They consequently do not disturb or injure the vessels as the dilitation balloon catheters do.

In sum, a structurally sound micro occlusion balloon catheter which blocks small vessels still does not exist. And a micro occlusion catheter which occludes and infuses a liquid and/or solid therapeutic and/or diagnostic agent is even more illusive. Yet the need for such catheters is ever increasing given the quest for noninvasive diagnostic and/or treatment procedures.

SUMMARY OF THE INVENTION

The aforementioned task is solved in a novel and elegant manner by providing for a micro occlusion balloon catheter and methods for use and manufacture thereof, comprising an elongate member having a proximal and a distal end and a first and second lumen connected to said proximal end. The first tureen communicates with an occlusion balloon located at the distal end of said elongate member. The second lumen extends the entire length of said elongate member and allows for the placement of the catheter over a guidewire. Second lumen 15, communicates with infusion opening 17, located distal to occlusion balloon 16. A further embodiment comprises a third lumen connected to the proximal end of said elongate member. Said third lumen may communicate with an infusion port located either proximally or distally to said occlusion balloon. In a still further embodiment the first lumen, the inflation/deflation balloon lumen, of the two lumen embodiment may be adapted to receive a removable stiffening stylet to ease insertion. In the three lumen embodiment, lumen one, the inflation/deflation balloon lumen, and/or the second or third infusion lumens may be proportioned so as to receive stiffening stylets.

These multi-lumen embodiments allow for the simultaneous task of occluding and infusing a therapeutic and/or diagnostic agent into vessels having a diameter ranging from about 1.5 to about 6 mm in diameter.

DETAILED DESCRIPTION OF THE INVENTION

Embodiments of the present invention are now described in detail with reference to the accompanying drawings. Occlusion Balloon 16, is illustrated in a deflated position throughout the drawings.

Figure 1:
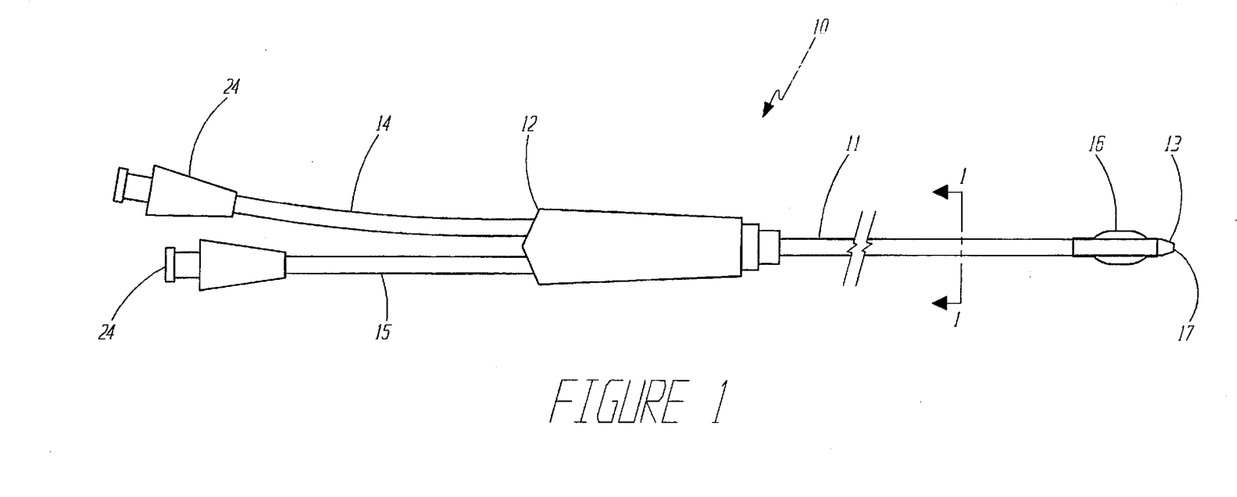
FIG. 1 is a plan view of a two lumen catheter in accordance with the present invention with distal infusion means.
Figure 7:
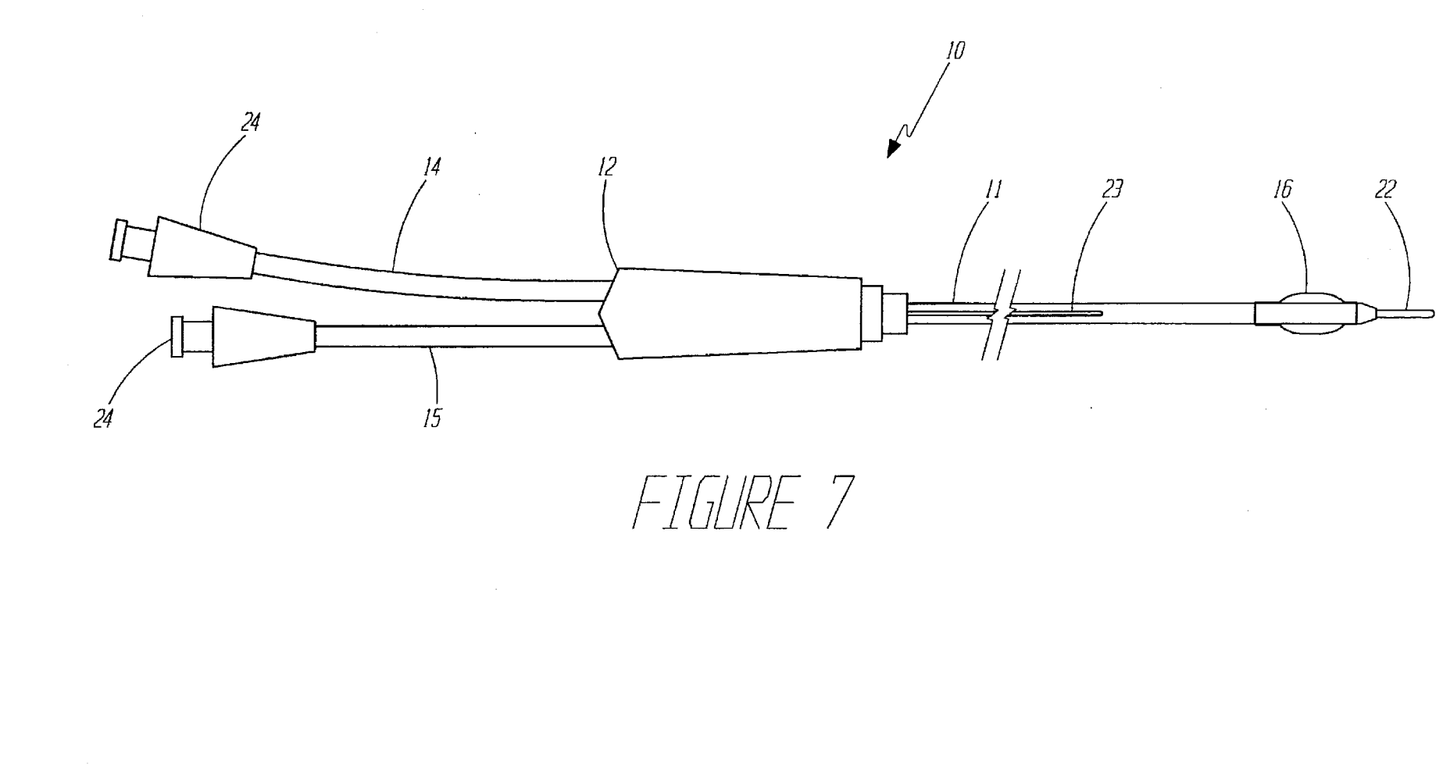
FIG. 7 is a plan view of a two lumen catheter in accordance with the present invention with the guidewire and removable stylet in place.

In reference to FIG. 1, catheter 10, comprises an elongate member 11, having a proximal end 12, and a distal end, 13, and a first lumen 14, and second lumen, 15, both connected to said proximal end 12. First lumen 14, extends the entire length of said elongate member 11 and communicates with an occlusion balloon, 16, located at distal end 13, of said elongate member 11. Second lumen 15, extends the entire length of said elongate member 11, and allows for the placement of catheter 10, over guidewire 22 (FIG. 7). Second lumen 15, communicates with an infusion opening, 17, located distal to occlusion balloon 16.

Figure 2A:
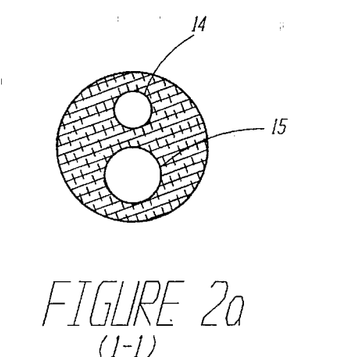
FIG. 2a is a cross sectional view taken along lines 1—1 in FIG. 1 which depicts an embodiment with circular lumens 14 and 15.
Figure 2B:
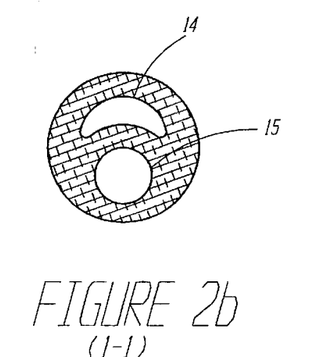
FIG. 2b is a cross sectional view taken along lines 1—1 in FIG. 1 which depicts an embodiment with a crescent shaped lumen 14 and a circular lumen 15.

FIG. 2a and FIG. 2b are crossectional view taken along line 1—1 further depicting lumen 14 and 15. In FIG. 2a lumens 14 and 15 are circular. In FIG. 2b lumen 14 is crescent shaped and lumen 15 is circular.

Figure 3:
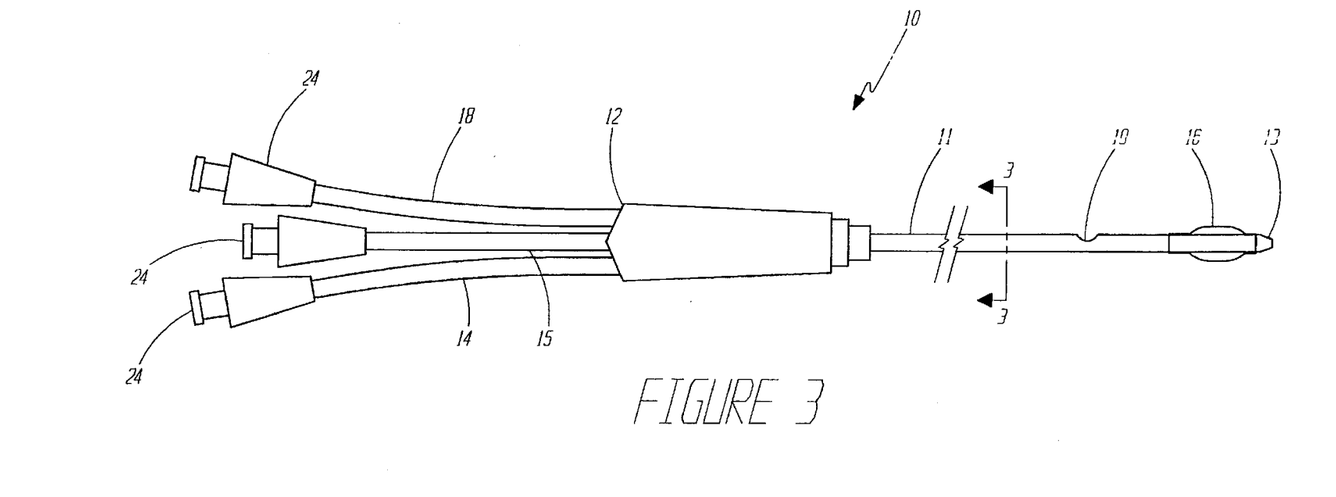
FIG. 3 is a plan view of a triple lumen catheter in accordance with the present invention with proximal and distal infusion means.
Figure 4A:
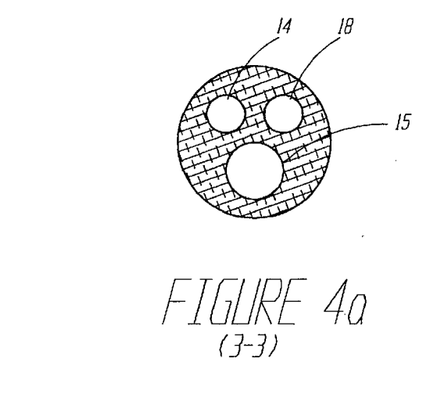
FIG. 4a is a cross sectional view taken along lines 3—3 in FIG. 3 which depicts an embodiment with circular lumens 14, 15, and 18.
Figure 4B:
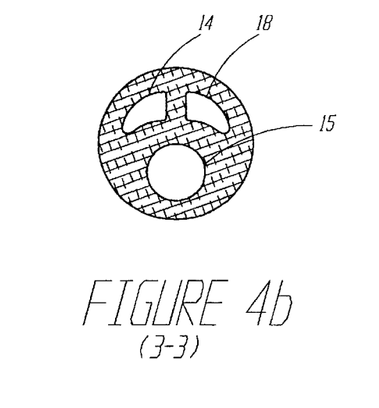
FIG. 4b is cross sectional view taken along lines 3—3 in FIG. 3 which depicts an embodiment with a circular lumen 15 and half-crescent-like lumens and 18.

FIG. 3, 4a and 4b depict a further embodiment comprising a third lumen, 18, connected to proximal end 12, of elongate member 11. Lumen 18 extends the entire length of said elongate member 11 and communicates with proximal infusion port 19 located proximally to occlusion balloon 16. This embodiment allows for simultaneous proximal and distal delivery of diagnostic and/or therapeutic agent(s) through lumen 15 and 18.

Figure 5:
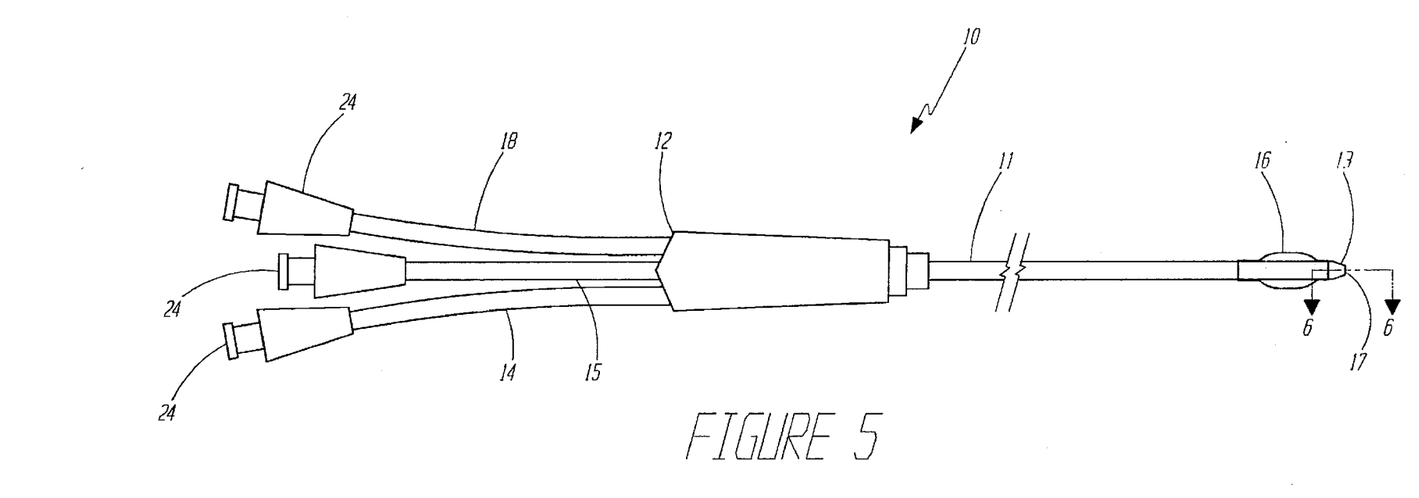
FIG. 5 is a plan view of a triple lumen catheter in accordance with the present invention with double distal infusion means.
Figure 6:
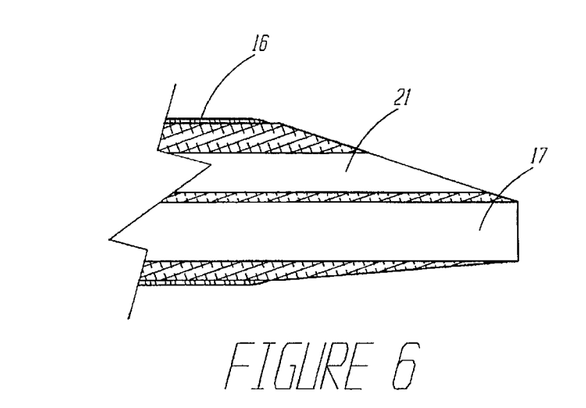
FIG. 6 is a cross sectional view taken along lines 5—5 in FIG. 5.

FIG. 5 and 6 depict respectively plan and cross sectional views of a still further embodiment advantageously allowing for double distal delivery. Lumen 18 communicates with distal infusion port 21 located distally to micro occlusion balloon 16 and adjacent to distal port 17 of lumen 15.

FIG. 4a and 4b depict variations of the embodiment shown in FIG. 3 wherein lumens 14, 15, and 18 are circular, as in FIG. 4a, or lumen 15 is circular and lumens 14 and 18 are half-crescent-like shaped, as in FIG. 4b.

Figure 8:
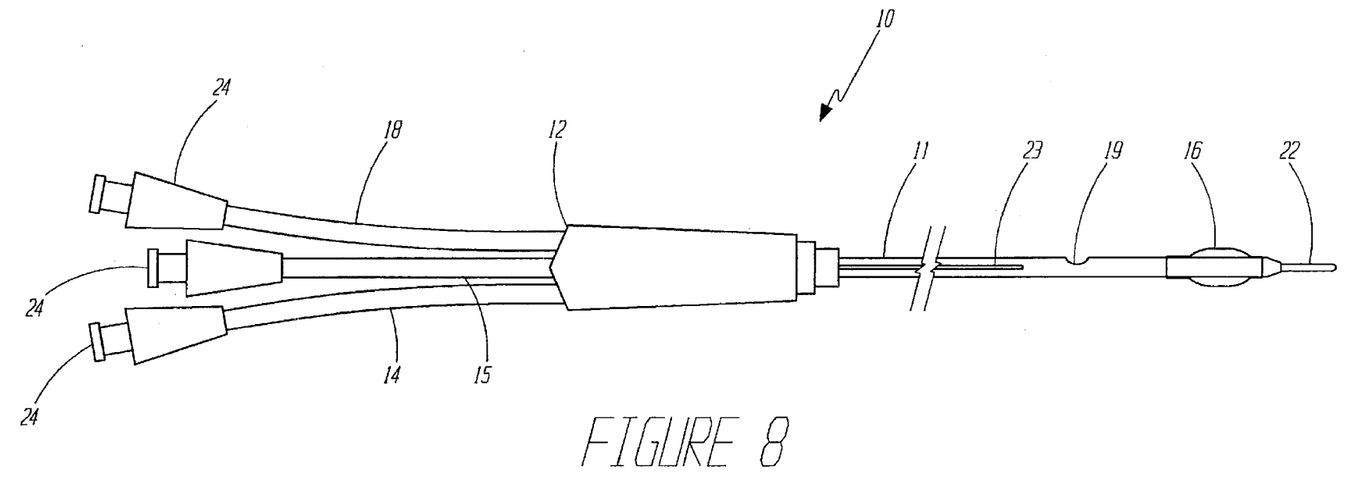
FIG. 8 is a plan view of a three lumen catheter in accordance with the present invention with one guidewire and two removable stylets in place.

FIG. 7 depicts a still further embodiment wherein lumen 14, the inflation/deflation balloon lumen, of the two lumen embodiment may be adapted to receive removable stiffening stylet, 23, to ease insertion by stiffening up the catheter shaft. Similarly FIG. 8 depicts the corresponding three lumen embodiment wherein lumen 14, the inflation/deflation balloon lumen, and/or infusion lumens 15 and 18 may be proportioned so as to receive stiffening stylet 23. The use of two removable stiffening stylets, 23, inserted in lumen 15 and 14 is shown in FIG. 8. Stiffening stylet(s) 23, are inserted to extend the length of member 11 until just proximal to infusion port 19, or occlusion balloon 16. The usual insertion is approximately 35 cm. If two stylets are used, the practitioner may however, insert one further than the other to vary the amount of stiffness as needed. Notably a guidewire 22, is present in both FIG. 7 and 8.

Lumen 14, 15 and 18 attach to luer connectors, 24, at their proximal end. Said luer connectors are then connected to syringes, valves etc. for the introduction of the therapeutic and/or diagnostic agents(s) and the balloon inflation media.

Figure 9:
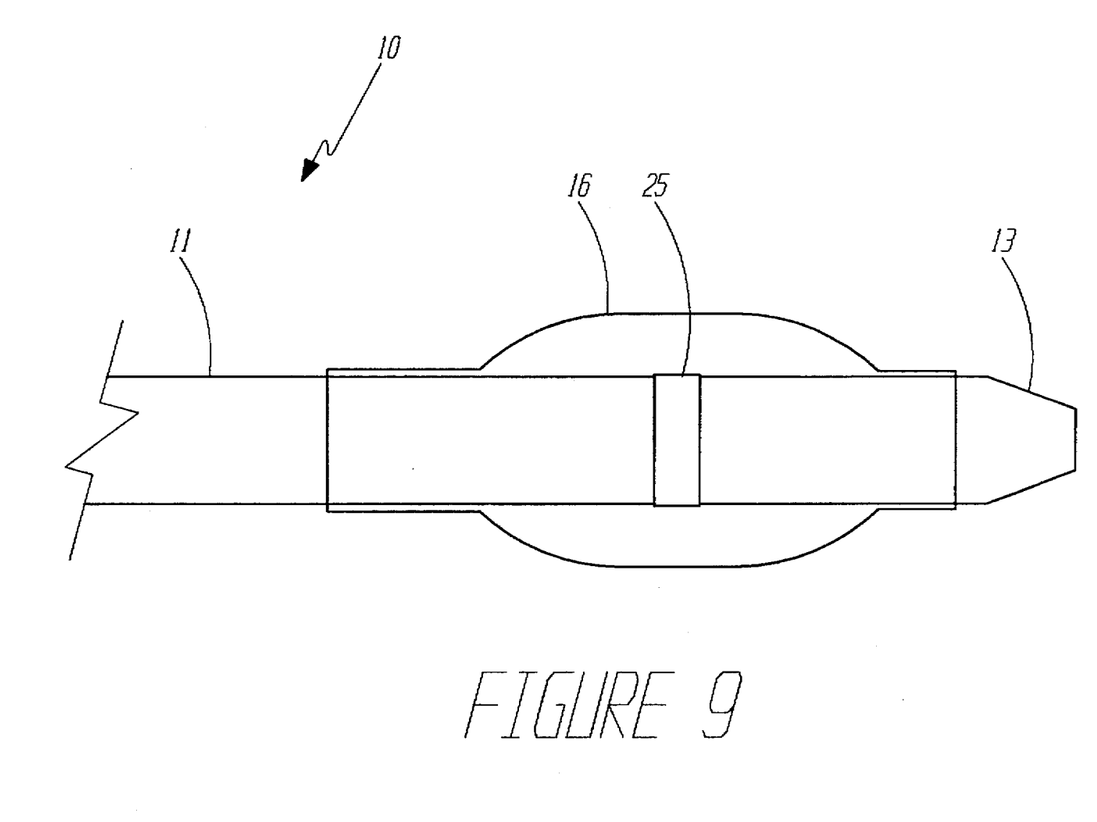
FIG. 9 is a plan view of the present invention incorporating a radiopaque marker.

FIG. 9 depicts a still further embodiment of the invention wherein elongate member 11, advantageously incorporates a radiopaque marker, 25. In FIG. 9 marker 25 is located under balloon 16, yet it may be located all along member 11, including distal end 13.

Micro occlusion balloon catheter 10 is manufactured via an extrusion process. Since extrusion processes are well known in the art, the general process is not discussed in detail except when it differs from those of the prior art.

In general, the extrusion process begins by heating the polymer until melted. The melted polymer is then forced under pressure through an extrusion tip and die. As the melted polymer exits the extrusion tip and die, it is cooled. A typical cooling method employs a water bath. The cooling step solidifies the device in the desired dimensions.

The particulars of the extrusion tip and die define the dimensions of the end product. In addition, the speed at which the tubing is pulled out of the extrusion tip also defines the shape of the end product. The present invention contemplates extrusion speeds from about 20 to about 45 cm/second.

The prior art extrusion process for catheter tubing employed a crosshead technique. In this technique the melted polymer is introduced into the side of the extrusion tip, flows around the interior sides of the extrusion tip and exits through the die. In contrast, the present invention employs an in-line process. The polymer is introduced at the back of the extrusion tip and flows in an approximately straight line through the die. The in-line technique allows for the manufacture of the novel micro size of the present invention.

Elongate member 11 and lumens 14, 15 and 18 may be manufactured of any of the commercially used catheter materials. Consequently, the selection of any one material constitutes no part of this invention. By way of illustration and not limitation mention may be made of polyethylene, polyamide, urethane, etc. polyethylene being particularly preferred. The specific material chosen will depend on the catheter's end use, the size of the vessel to be invaded, and whether or not a stylet or stylets will be used to assist during insertion and advancement. In other words the desired end use will dictate the stiffness, flexibility, strength and slipperiness of the material.

Similarly, occlusion balloon 16, may be manufactured of any of the commercially known occlusion balloon materials. By way of illustration and not limitation mention may be made of latex, silicone, ethylvinylacetate, urethane etc. Latex or silicone being particularly preferred.

The material for elongate member 11, lumens 14, 15 and 18, and occlusion balloon 16 may contain any one or more of the following additives. By way of illustration and not limitation mention may be made of radiopaque fillers, slip additives, hydrophilic coatings, etc. Silicon being the preferred hydrophilic coating.

Dimensionally speaking, catheter 10 is preferably from about 100 cm to about 250 cm in length. The end use again dictating the specific length. By way of illustration and not limitation a cerebral vasculature application may warrant a catheter length from about 100 to about 150 cm, 150 cm being particularly preferred; a coronary vasculature application may warrant a catheter length from about 100 to about 155 cm in length, 135 cm being particularly preferred; a peripheral vasculature application may warrant a catheter length from about 70 to about 100 cm in length, 80 cm being particularly preferred; a renal vasculature application may warrant a catheter length from about 60 to about 90 cm in length, 70 cm being particularly preferred; and a hepatic vasculature application may warrant a catheter from about 70 to about 100 cm in length, 80 cm being particularly preferred.

Elongate member 11's outer diameter may range from about a 2 to about a 3 French i.e. from about 0.6 mm to about 1.0 mm. Elongate member 11 may also be a 3 French at its proximal end and taper into a 2.5 French at its distal end. The end use again dictating the specific dimensions. Elongate member 11's inner diameter may range from about 0.014 inches to about 0.023 inches. If elongate member 11 is to receive a guidewire 22, it will need to be proportioned accordingly. The present invention contemplates use of guidewires up to 0.018 inches in diameter. The ability to accomodate guidewires affords the present invention many advantages. Among them steerability through geometrically tortuous paths, ability to advance the catheter in low or no-flow vessels, ability to deliver a wide range of liquid and variably sized and shaped solids, increased injection pressure tolerance and hence decreased catheter related rupture.

Distal end 13, may or may not be tapered. If tapered, occlusion balloon 16, is preferrably attached in such a way that the diameter of the deflated balloon closely approximates the diameter of elongate member 11. This configuration assures maximum distal lumen size and low profile. Occlusion balloon 16, is advantageously expandable up to 6–8 mm The present invention is specifically designed to accomodate vessels ranging from about 1.5 to about 6 mm in diameter. By way of illustration and not limitation, specific contemplated vessels may include cerebral, coronary, peripheral, renal, and hepatic vasculatures; ureters, fallopian tubes, the gastrointestinal tract, etc.

In general, occlusion balloon catheters are introduced via a cutdown of the vasculature or percutaneously via an introducer sheath yet the choice of entry is largely controlled by the specific procedure and the physician's preference. The catheter is advanced and positioned in the desired area under fluoroscopic guidance. Specifically the catheter is delivered over a guidewire to the desired location. Positioning may also be aided by the use of 1 or two removable stylets inserted into lumen 15 and/or 14 or 18. Once positioned the stylet(s), and guidewires if desired are removed and the balloon is inflated by means of a hand held syringe or other means to occlude blood flow. In the two lumen emodiment diagnostic and/or therapeutic agent(s) are delivered through the guidewire lumen 15. The standard inflation medium is a 1:2 mixture of contrast medium and normal saline.

In the three lumen proximal and distal delivery embodiment, the diagnostic and/or therapeutic agent(s) may be delivered through proximal port 19, of infusion lumen 18, and distal port 17 of guidewire lumen 15. In the double distal delivery embodiment diagnostic and/or therapeutic agent(s) may be delivered through distal port 21 of lumen 18 and distal port 17 of guidewire lumen 15.

When the procedure is completed, the balloon is deflated by applying suction to the balloon lumen. Once deflated, micro occlusion balloon 16, may be advanced to another treatment site or removed from the vessel. A guidewire may be reinserted prior to the removal process to assist removal.

Micro occlusion balloons are generally indicated for use for temporary vessel occlusion in applications including but not limited to arteriography, preoperative occlusion and control of hemorrhage. The present invention's additional capability of delivering diagnostic and/or therapeutic agent (s) is much desired for non-invasive or minimally invasive visualization and/or treatment procedures. For diagnostic applications mention may be made of arteriograms, venograms, pressure monitoring, etc.

More specifically, the present invention finds treatment use whenever site specific treatment is warranted. For site specific applications mention may be made of the administration of chemotherapeutic agents, embolic, thrombolytic agents, etc. For embolic agents mention may be made of ethanol, polyvinyl acetate particles, coils, glue, gel foam etc. For thrombolytic agents mention may be made of streptokinase, urokinase, tissue plasminogen activator, etc. For chemotherapeutic agents mention may be made of adriamyacin, mitramyacin, cistplatnin, etc. For typical diagnostic devices mention may be made of optical fibers, electrodes, thermal elements, etc.

Yet not only does the present invention allow for diagnostic and treatment uses, it advantageously allows for the simultaneous administration of diagnostic and therapeutic agents. Thus by way of illustration and not limitation a diagnostic agent may be released during insertion and advancement to assure proper placement of the catheter, and once placed a therapeutic agent may be released to treat the specific site. Even more advantageously the triple lumen embodiment allows for the multiple administration of diagnostic and/or therapeutic agent(s). Thus by way of illustration and not limitation a drug may be administered via one infusion lumen while the second infusion lumen is ready to infuse a secondary agent if indicated. Thus any time a synergistic or antidotal intervention is warranted, as is often the case in medicine, the present invention may be used.

The many advantages of using a micro occlusion balloon catheter in accordance with the aforementioned general procedures and uses is clearly evidenced by the following specific applications. The micro occlusion balloon catheters of the present invention enhance the selectivity and quality of arteriography and venography. In renal venograms these novel catheters stop blood from flowing away from the kidney in a vein and thereby provide the dye, which is injected against the flow of blood, a greater chance of reaching peripheral areas. The small size of the novel catheter greatly enhances radiologic visualization by providing for the placement of the catheter in smaller vessels. Thus small vessels are visualizable by the present invention which have heretofore never been visualized.

Similarly renal arteriograms are enhanced by allowing insertion into small diameter vessels which have heretofore never been penetrable. In the three lumen distal and proximal delivery embodiment, visualization is further enhanced by the ability to deliver the dye proximally and distally to the balloon.

The novel mico occlusion balloon catheter may also be used for the preoperative occlusion of blood supply to specific organs. In the case of the removal of an organ e.g. a nephrectomy, the novel micro occlusion balloon catheter may be inserted prior to surgery to stop all arterial circulation to the kidney. This method will severly decrease blood loss and hence reduce recovery time.

The emergency control of hemorrhaging may also be further controlled by the use of the novel catheter. Notably, the use of a catheter in this situation is only to block the leaking vessels i.e. to stabilize until surgical treatment can be performed. Two competing factors are at play when controlling hemorrhaging. One is to block the vessel and the other is to do so as selectively as possible to prevent oxygen debt to unaffected tissue. The unique size of the present catheter allows for minimal oxygen debt by allowing for the smallest blockage via penetratability of the smallest vessels necessary to prevent hemorrhaging. In other words, large vessels need not unnecessarily be blocked as was the case with the prior art balloon catheters which did not fit into small vessels. This is particularly advantageous with cerebral, neck and aortic aneurysms, a special type of hemorrhage. Aneurysms are associated with a high mortality rate. The novel micro occlusion balloon catheters of the present invention allow for placement within the small cerebral and neck vasculature heretofore unattainable.

The novel catheters of the present invention may also be used to to increase the selectivity of administering anticancer drugs directly to afflicted organs. The ability to specifically target the neoplastic area is very desirable given the toxicity of chemotherapeutic drugs. The present invention's size as well as ability to occlude blood flow, decrease exposure to toxins.

The novel catheter may also be useful for the administration of embolic agents to stop bleeding. If the administration of vasoconstrictive drugs is unsuccessful, the bleeding can often only be stopped by delivering a clotting agent directly into the vessel. Clotting agents may include but are not limited to autologous tissue, gelatin sponges, oxygel, silicon rubber compounds cyano-acrylates, Ivalon, metal or silastic spheres, trans-catheter electro coagulation, metalic devices such as the Gianturco coil, etc. The risk with injecting clotting agents is that they may reflux and go into another vessel. The present invention balloon catheter advantageously alleviates this risk. In addition, the micro size of the novel catheter allows for more direct administration of the clotting agents by enabling advancement into small vessel never heretofore penetratable.

A still further vascular application is the occlusion of vessels to prevent nutrient supply to tumors in an attempt to arrest their growth. Again there are competing interests which are nicely solved by the present invention. While the occlusion balloon blocks blood supply to the tumor the micro size of the catheter assures that only a very small area is left unnourished.

By way of recapitulation, the present invention comprises a novel micro occlusion balloon catheter having double and triple lumen embodiments. Said novel catheters advantageously allow for penetration of minute vessels and thus allow for target specific blockage and delivery of diagnostic and/or therapeutic agents. Said delivery may advantageously be distal, distal and proximal, or double distal.

Since certain changes may be made without departing from the scope of the invention as described herein it is intended that all matter described in the foregoing specification, including the drawings, shall be interpreted as illustrative and not in a limiting sense.

We claim:

1. A method of delivering a therapeutic agent or diagnostic device into a vessel having a diameter from about 1.5 mm to about 6.0 mm which comprises:

introducing a guide wire into a vessel;

introducing a micro occlusion balloon catheter having
 a proximal end,
 a distal end,
 an inflatable micro occlusion balloon attached to the distal end of the balloon catheter and in fluid communication with the proximal end of the balloon catheter via a balloon inflation lumen within the balloon catheter,
 an infusion lumen making a fluid path between the proximal end of the balloon catheter and a distal opening proximal to the balloon,
 and a guide wire lumen from the proximal end of the balloon catheter to a distal opening distal to the balloon, wherein the infusion lumen and the inflation lumen are adapted to receive stiffening stylets,
 into the vessel and over the guide wire;

inserting stiffening stylets into the infusion lumen and into the inflation lumen before or while introducing the micro occlusion balloon catheter into the vessel;

varying the stiffness of the micro occlusion balloon catheter, by inserting one of the stiffening stylets farther into the micro occlusion balloon catheter than the other, as the micro occlusion balloon catheter is advanced over the guide wire; and removing the stiffening stylets once the micro occlusion balloon is adjacent a treatment site;

inflating the micro occlusion balloon;

removing the guide wire;

delivering a therapeutic agent or diagnostic device through the infusion lumen;

delivering a therapeutic agent or diagnostic device through the guide wire lumen;

deflating the micro occlusion balloon; and removing the micro occlusion balloon catheter from the vessel.

2. A method of delivering a therapeutic agent or diagnostic device into a vessel having a diameter from about 1.5 mm to about 6.0 mm which comprises:

introducing a guide wire into a vessel;

introducing a micro occlusion balloon catheter having
- a proximal end,
- a distal end,
- an inflatable micro occlusion balloon attached to the distal end of the balloon catheter and in fluid communication with the proximal end of the balloon catheter via a balloon inflation lumen within the balloon catheter,
- an infusion lumen making a fluid path between the proximal end of the balloon catheter and a distal opening proximal to the balloon,
- and a guide wire lumen from the proximal end of the balloon catheter to a distal opening distal to the balloon, wherein the infusion lumen and the inflation lumen are adapted to receive stiffening stylets, into the vessel and over the guide wire;

inflating the micro occlusion balloon;

removing the guide wire:

delivering a therapeutic agent or diagnostic device through the infusion lumen wherein the therapeutic agent is an embolic agent selected from the group consisting of ethanol, polyvinyl acetate particles, coils, glue and gel foam;

delivering a therapeutic agent or diagnostic device through the guide wire lumen wherein the therapeutic agent is an embolic agent selected from the group consisting of ethanol polyvinyl acetate particles, coils, glue and gel foam;

deflating the micro occlusion balloon; and removing the micro occlusion balloon catheter from the vessel.

3. A method of delivering a therapeutic agent or diagnostic device into a vessel having a diameter from about 1.5 mm to about 6.0 mm which comprises:

introducing a guide wire into a vessel;

introducing a micro occlusion balloon catheter having
- a proximal end,
- a distal end,
- an inflatable micro occlusion balloon attached to the distal end of the balloon catheter and in fluid communication with the proximal end of the balloon catheter via a balloon inflation lumen within the balloon catheter,
- an infusion lumen making a fluid path between the proximal end of the balloon catheter and a distal opening proximal to the balloon,
- and a guide wire lumen from the proximal end of the balloon catheter to a distal opening distal to the balloon, wherein the infusion lumen and the inflation lumen are adapted to receive stiffening stylets, into the vessel and over the guide wire;

inflating the micro occlusion balloon;

removing the guide wire;

delivering a therapeutic agent or diagnostic device through the infusion lumen wherein the therapeutic agent is an thrombolytic agent selected from the group consisting of streptokinase, urokinase, and tissue plasminogen activator;

delivering a therapeutic agent or diagnostic device through the guide wire lumen wherein the therapeutic agent is an thrombolytic agent selected from the group consisting of streptokinase, urokinase, and tissue plasminogen activator;

deflating the micro occlusion balloon; and removing the micro occlusion balloon catheter from the vessel.

* * * * *

UNITED STATES PATENT AND TRADEMARK OFFICE
CERTIFICATE OF CORRECTION

PATENT NO. : 5,637,086
DATED : June 10, 1997
INVENTOR(S) : FERGUSON et al.

It is certified that error appears in the above-identified patent and that said Letters Patent is hereby corrected as shown below:

At column 2, line 63, "tureen" should be --lumen--.

At column 3, line 35, change "lumens and 18" to --lumens 14 and 18--.

At column 4, line 12, after "15 and 18", insert --FIG. 4a and 4b depict variations of the embodiment shown in FIG. 3 wherein lumens 14, 15 and 18 are circular, as in FIG. 4a, or lumen 15 is circular and lumens 14 and 18 are half-crescent-like shaped, as in FIG. 4b.--

At column 4, delete lines 18-21 in their entirety (beginning with "FIG. 4a and 4b...").

At column 6, line 3, insert --.-- after "mm"; at lines 43-44, "agent (s)" should be --agent(s)--.

At column 9, line 37, claim 2, "removing" should start a new paragraph.

At column 10, line 35, claim 3, "removing" should start a new paragraph.

Signed and Sealed this

Eighth Day of December, 1998

*Attest:*

BRUCE LEHMAN

*Attesting Officer*   *Commissioner of Patents and Trademarks*